(12) United States Patent
Linnau et al.

(10) Patent No.: US 6,395,880 B1
(45) Date of Patent: May 28, 2002

(54) METHOD FOR PURIFICATION OF ANTITHROMBIN III USING AN ANION EXCHANGER

(75) Inventors: Yendra Linnau; Ernst Hetzl; H. Peter Matthiessen; Silvia Neppl, all of Vienna; Wolfgang Schönhofer, St. Pölten; Hans-Peter Schwarz, Vienna, all of (AT)

(73) Assignee: Baxter Aktiengesellschaft, Vienna (AT)

( * ) Notice: Subject to any disclaimer, the term of this patent is extended or adjusted under 35 U.S.C. 154(b) by 0 days.

(21) Appl. No.: 09/509,052

(22) PCT Filed: Sep. 17, 1998

(86) PCT No.: PCT/AT98/00223

§ 371 (c)(1),
(2), (4) Date: May 19, 2000

(87) PCT Pub. No.: WO99/15562

PCT Pub. Date: Apr. 1, 1999

(30) Foreign Application Priority Data

Sep. 19, 1997 (AT) ............................................... 1594/97

(51) Int. Cl.⁷ .......................... C12N 9/74; A61K 35/14; A23J 11/00
(52) U.S. Cl. ...................... 530/393; 530/412; 530/416; 435/214
(58) Field of Search ................................ 530/393, 412, 530/416; 435/214

(56) References Cited

U.S. PATENT DOCUMENTS 4,286,056 A * 8/1981 Andary et al. ................. 435/3
4,510,084 A * 4/1985 Eibl et al. .................... 530/393
4,540,573 A 9/1985 Neurath et al. ................ 424/85
5,319,072 A * 6/1994 Uemura et al. ............. 530/393

FOREIGN PATENT DOCUMENTS

| DE | 22 43 688 C3 | 3/1973 |
| DE | 44 34 538 A1 | 4/1995 |
| EP | 0 131 740 A2 | 1/1985 |
| EP | 0 159 311 A1 | 10/1985 |
| EP | 0 252 392 A2 | 1/1988 |
| EP | 0 307 002 A1 | 3/1989 |
| EP | 0 519 901 A2 | 12/1992 |
| WO | WO 94/13329 | 6/1994 |

OTHER PUBLICATIONS

Clement, L.T., "Purification and Characterization of Guinea Pig Antithrombin III", *Prep. Biochem.*, vol. 13, 1983, pp. 1–21.

Miller–Anderson, M. et al., "Purification of Antithrombin III by Affinity Chromatography", *Thromb. Res.*, vol. 5, 1974, pp. 439–452.

\* cited by examiner

*Primary Examiner*—David M. Naff
*Assistant Examiner*—Mike Meller

(57) ABSTRACT

A method of purifying antithrombin III (AT III) from a starting material containing an AT III/heparin complex or an AT III/heparinoid complex is disclosed. First, the method comprises adsorbing the AT III/heparin complex or the AT III/heparinoid complex on an anion exchanger material. Second, the method involves separating the AT III from the adsorbed AT III/heparin complex or an AT III/heparinoid complex by elution with a buffer having a pH ranging from 8.5 to 10.5 and a conductivity between 10 and 60 mS.

12 Claims, No Drawings

METHOD FOR PURIFICATION OF ANTITHROMBIN III USING AN ANION EXCHANGER

FIELD OF INVENTION

The invention relates to a new method for purifying antithrombin III.

BACKGROUND OF THE INVENTION

Antithrombin III (AT III) is a plasmatic protein which acts as a coagulation inhibitor by inhibiting thrombin, factors IXa, Xa, XIa and XIIa.

AT III deficiency or hereditary thrombophilia is an autosomal dominant hereditary disease with an inclination to thrombosis and embolisms due to a reduced formation of AT III.

Acquired AT III deficiency may, e.g., occur with disseminated intravascular coagulation (DIC), sepsis, cirrhosis of the liver or with nephrotic syndrome.

AT III-deficiency symptoms may also occur in case of heart-valve prostheses, postoperative thromboembolic complications, in estrogen therapy or in the asparaginase therapy.

AT III has a high affinity to heparin and heparinoids, and therefore a separation of the heparin or the heparinoid is necessary when producing pure antithrombin III-preparations.

According to EP 0 307 002 A1, the cleavage of this AT III/heparin or AT III/heparinoid complex, respectively, is carried out with immobilized protamin, whereby heparin is bound to immobilized protamin, and AT III is recovered from the supernatant. Prior to the treatment with the immobilized protamin, the AT III/heparin or AT III/heparinoid complex, respectively, is purified from undesired proteins by adsorption on an ion exchanger and elution by means of a saline solution at pH 7.5. It has been shown that with the ion exchange chromatography not a cleavage of the complex, but a separation of undesired accompanying proteins was achieved, the complex as such remaining adsorbed without any change.

A further possible way of purifying AT III is by means of affinity chromatography via heparin-sepharose.

In Prep. Biochem. 13 (1) (1983), pp. 1–20, e.g., a method for purifying AT III is described in which AT III at first was purified via affinity chromatography with heparin-sepharose, and subsequently by means of ion exchange chromatography and gel chromatography, the elution of AT III from heparin-sepharose occuring at pH 7.4. The ion exchange chromatography was carried out on DEAE-Sepharose, AT III being bound at a pH of 8.6.

In Thrombosis Research 5 (1974), pp. 431–452, also the purification of AT III via heparin-sepharose is described, adsorption being attained at pH 8.5 and desorption, i.e. the cleavage of the complex of immobilized heparin and AT III, at pH 7.5. In the subsequent ion exchange chromatography on DEAE-Sephadex, AT III was bound at pH 8.0 and eluted at pH 7.4.

A similar method is described in DE 2 243 888; here, too, the purification of AT III on a cross-linked heparin-agarose gel is disclosed, wjereby the adsorption on the heparin gel is carried out at pH 8.5, and the desorption, i.e. the cleavage of AT III from immobilized heparin, at pH 7.3.

BRIEF SUMMARY OF THE INVENTION

The present invention is based on the object of providing a new method for producing antithrombin III-preparations with high purity and in high yields, whereby AT III, as free as possible from heparin and heparinoid, respectively, is to be recovered.

DETAILED DESCRIPTION OF THE INVENTION

According to the invention, this object is achieved by a method for purifying AT III from a starting material comprising an AT III/heparin or At III/heparinoid complex, which is characterized in that the AT II/heparin or AT III/heparinoid complex is adsorbed on an anion exchanger material, and subsequently AT III is cleaved from the adsorbed complex and eluted. At this cleavage, heparin remains on the anion exchanger, i.e. a selective elution of AT III occurs.

Preferably, the cleavage according to the invention is carried out with a buffer at a pH ranging from 8.5 to 10.5.

For, surprisingly, it has been found that cleavage of the heparin/AT III or heparinoid/AT III complex, respectively, is possible in the course of an anion exchange chromatography, and this even at a pH higher than 8.5.

It has been found that AT III can be eluted from an anion exchanger selectively relative to heparin or that the complex formation between AT III and heparin or heparinoid, respectively, can be broken, while simultaneously the binding of heparin to the adsorption material (which binding in contrast to heparin-sepharose is not covalent) will remain. Although in the prior art the affinity of AT III to heparin has been considered to be very high, primarily at such a pH, (cf. Thrombosis Research (1974) or DE 2 243 688) and the cleavage of the complex (i.e. the cleavage of AT III from immobilized heparin), even with covalently bound heparin, was always carried out at low pH values, it has been shown that by means of anion exchange chromatography, a selective elution of AT III from adsorbed AT III/heparin or AT III/heparinoid complex is possible.

Within the scope of the present invention it has however been found that, even at such high pH-values, a cleavage of the complex could be attained, with heparin nevertheless remaining substantially bound to the anion exchanger.

Preferably, in the method according to the invention, elution is carried out with a buffer which has a conductivity of between 15 and 50 mS. At such a conductivity, an optimum of specificity of elution is attained, i.e., that it will be sufficient, on the one hand, to allow a substantially complete cleavage of the complex, while, on the other hand, it is not that high that also the heparin or heparinoid, respectively, will be co-eluted. The conditions for the adsorption and desorption, respectively, generally depend on the anion exchange material used and substantially are a function of the conductivity and of the pH value of the buffer.

In particular, the correlation between pH and the conductivity is such that with a low conductivity, e.g. around 20 mS, also the pH of the buffer solution can be lower, e.g. 8.5, and vice versa. As the buffer, e.g. Tris-, phosphate-, or glycine-containing solutions are used.

Preferably, prior to adsorption, heparin or a heparinoid, respectively, in an amount of between 30 and 3,000 U/ml is admixed. This will ensure that all the AT III in a starting material will be present as a complex, and thus no loss of yield caused by free AT III will occur.

Preferably, the method according to the invention is carried out in a two-step chromatographic purification, wherein, in a first step, the complex is adsorbed on an anion exchanger material, and at a pH in the range of from 6.0 to 7.5 the stable complex is eluted. Subsequently the adsorption of the complex according to the invention and the cleavage respectively the elution of AT III from the complex occur. With a pH value of between 8.5 and 10.5, preferably a higher conductivity of the buffer is adjusted, e.g. 10–60 mS, preferably between 15–50 mS, most preferred between 20–35 mS, at the elution.

Since AT III preferably is used as a therapeutic agent, in most instances a treatment for virus inactivation is necessary. This treatment preferably is carried out at the stage of the AT III/heparin or AT III/heparinoid complex, since AT III in complexed form is more stable than in free form. Preferably, the virus inactivation treatment is also carried out in two steps, i.e. by two independent virus inactivation methods.

This inactivation treatment preferably is ensured by a tenside and/or heat treatment, e.g. a heat treatment in the solid state, in particular a vapor treatment according to EP-0 159 311, EP-0 519 901 or EP-0 674 531.

Further methods for inactivation of viruses also comprise the treatment by chemical or chemical/physical methods, e.g. with chaotropic substances according to WO 94/13329, DE 44 34 538 or EP-0 131 740 (solvent) or photoinactivation.

Nanofiltration also constitutes a preferred method for depleting viruses within the scope of the present invention.

As the anion exchanger, in principle, all anion exchangers may be used which have an affinity to heparin or heparirolds, such as, e.g. cellulose-based anion exchangers with diethylaminoethyl-groups (DEAE-Sephacell®, DE32, DE52 and the like or Express Ion D; all from Whatman) or with $CH_2N^+$ $(CH_3)_3$ groups (QA52 or Express Ion Q; from Whatman), anion exchangers based on cross-linked dextrane with diethylaminoethyl groups (DEAE-Sephadex®), agarose-based an on exchangers with diethylaminoethyl groups (DEAE-Sepharose CL6B®, DEAE-Sepharose Fast Flow®), anion exchangers based on cross-linked dextrane with diethyl-[2-hydroxypropyl]aminoethyl groups (QAE-Sephadex®), anion exchangers based on agarose with $CH_2N^+$ $(CH_3)_3$ groups (Q-Sepharose Fast Flow®, Q-Sepharose High Performances®, Q-Sepharose Big Beads®) or copolymers of agarose and dextrane (Q-Sepharose XL) (all from Pharmacia), spherical chromatographic gels, prepared by copolymerisation of N-acryloyl-2-amino-2-hydroxymethyl-1,3-propanediol and an anionic acryl derivative with diethylamino-ethyl groups as functional anion exchanger (DEAE-Tris-Acryl®), non-compressible silica-dextrane matrices wherein a porous silica gel is embedded in a cross-linked dextrane matrix, with reactive diethylaminoethyl anion exchanger groups (DEAE-Spherodex®), gels from rigid polystyrene particles, whose pores are filled with a hydrogel, which carries quaternary amine groups having strong anion exchanger activity (Q-Hyper-D®) (all from Sepracor); rigid macroporous hydrophilic surfaces with $N^+$ $(C_2H_5)_2$ or $N^+$ $(CH_3)$ groups (Macroprep DEAE®, Macroprep Q® (all from BioRad); anion exchangers with diethylaminoethyl-diethyl-(2-hydroxypropyl)-aminoethyl and $CH_2N^+$ $(CH_3)_3$-groups (DEAE-Toyopearl®, QAE-Toyopearl®, Toyopearl Super-Q® (all from Tosohaas), anion exchanger resins consisting of porous polymethacrylate/polyacrylate gel (protein PAK DEAE®, from Waters); anion exchangers based on copolymers consisting of oligoethyleneglycol-dimethylacrylate, glycidyl-methacrylate and pentaerythritol-dimethylacrylate with a hydrophobic surface (Fractogel EMD-TMAE®, Fractogel EMD-DEAE®, Fractogel EMD-DMAE®), anion exchangers based on silica gel with porous spherical pressure-stable chromatography particles (Licrospher 1000 TMAE®, Licrospher 1000 DEAE® and Licrospher 4000 DMAE®) (all from MERCK).

In a particularly preferred embodiment of the method according to the invention, human plasma or an AT III-containing plasma fraction is admixed with heparin or a heparinoid, an AT III/heparin or AT III/heparinoid complex being formed, and this complex is subjected to a heat treatment for inactivation of infectous agents. This treatment optionally is carried out in the presence of stabilizing organic polyvalent salts, such as, e.g., citrate and/or ammonium sulfate, and preferably at a temperature in the range of from 40 to 70° C. for a period of time of between 3 and 30 hours, treatment at a temperature of around 60° C. for approximately 10 hours being particularly preferred.

In the method according to the invention preferably it is departed from human plasma or from a [human] plasma fraction containing AT III, preferably from cryoprecipitate-poor plasma, or from a Cohn-fraction, preferably from a Cohn-fraction IV.

The present invention will be explained in more detail by way of the following examples without, however, being restricted thereto.

EXAMPLE 1

93.2 l of cryoprecipitate-poor plasma were admixed with $7.5 \times 10^6$ U of heparin, stirred for ½hour, and 1 g of DEAE-Sephadex A50 (from Pharmacia) was admixed per liter. By separating the gel and subsequent removal of non-bound proteins by means of a citrate-buffered NaCl solution (1 g/l NaCl, pH 7.5), the AT III/heparin complex was recovered by elution with a buffer solution which has a conductivity of 44 mS and a pH of.7.5.

Subsequently, the solution was heated for 10 hours at 60° C. in the presence of stabilizing organic polyvalent salts (160 g/l Na-citrate) so as to inactivate possibly present pathogenic microorganisms.

The precipitate formed was separated by centrifugation or filtration and discarded. The clear solution was rebuffered to pH 9.0 and to a conductivity of 12.2 mS. The AT III/heparin complex was bound on a chromatographic column consisting of 1,000 ml Q-Sepharose Fast Flow® (from Pharmacia), and AT III was selectively eluted by means of a buffer solution at pH 9.0 and a conductivity of 26 mS.

| Results | AT III U/ml | Heparin U/ml | AT III/Protein |
|---|---|---|---|
| DEAE-Sephadex-Eluate | 7.3 | 30.5 | 1.6 U/mg |
| Q-Sepharose-Eluate | 7.2 | 0.5 | 3.9 |

EXAMPLE 2
(At Present Considered by Applicant to be the Best Mode of Carrying Out the Invention)

24.5 l of plasma were admixed with $1.85 \times 10^6$ U of heparin after removal of the cryoprecipitate and of the prothrombin complex. 15 g of DE 52 cellulose (from Whatman) per liter were used to adsorb the AT III/heparin complex, and the product was recovered by elution with a buffer solution which had a conductivity of 45 mS and a pH of 8.0. After pasteurizing (60° C., 10 hours) the solution was rebuffered and treated with Triton®×100 (polyethyleneglycol-tert.octylphenylether, Tween® 80 (polyoxyethylenesorbitan-mono-oleate) as well as tri(n-butyl)phosphate (TNBP) at 25° C. according to U.S. Pat. No. 4,540,573.

The AT III was chromatographically purified via a 25 ml Q-Sepharose Fast-Flows column (from Pharmacia) and recovered by elution with a buffer solution at pH 9.8 and with a conductivity of 23 mS. By ultrafiltration and diafiltration, the AT III was adjusted to 100 U/ml, subsequently it was tilled in containers by filtration in a sterile condition, and, optionally, freeze-dried.

| Results after freeze-drying: | |
| --- | --- |
| AT III: | 96 U/ml |
| Heparin: | 0.8 U/ml |
| AT III/protein: | 6.2 U/mg |
| Triton, Tween, TNBP: | < detection limits |
| Heparin binding of AT III: | >95%*) |

*) according to Europ. Pharmacopeia

EXAMPLE 3

Example 2 was repeated, yet Toyopearl® Q-650 Th® (Toso Haas) was used instead of Q-Sepharose.

| Result (eluate): | |
| --- | --- |
| AT III: | 4.5 U/ml |
| Heparin: | 0.1 U/ml |
| AT III/protein: | 3.2 U/mg |

EXAMPLE 4

Example 2 was repeated, yet Express Ion Q (Whatman) was used instead of Q-Sepharose.

| Result (eluate): | |
| --- | --- |
| AT III: | 8.0 U/ml |
| Heparin: | 0.8 U/ml |
| AT III/protein: | 5.5 U/mg |

What is claimed is:

1. A method for purifying antithrombin III AT III from a starting material containing an AT III/heparin complex or an AT III/heparinoid complex, said method comprising adsorbing said AT III/heparin complex or said AT III/heparinoid compelx on an anion exchanger material and, subsequently, separating AT III from said absorbed AT III/heparin complex or said AT/III heparinoid complex by elution with a buffer having a pH ranging from 8.5 to 10.5 and a conductivity between 10 and 60 mS.

2. A method as set forth in claim 1, wherein said buffer for said elution has a conductivity of between 15 and 50 mS.

3. A method as set forth-in claim 1, wherein said buffer for said elution has a conductivity of between 20 and 35 mS.

4. A method as set forth in claim 1, wherein a heparin or a heparinoid in an amount of between 30 and 3000 U/ml is admixed with an AT III-containing material, whereupon said AT III/heparin complex or said AT III/heparinoid complex as starting material is formed.

5. A method as set forth in claim 1, wherein said AT III/heparin complex or said AT III/heparinoid complex is obtained by adsorbing said AT III/heparin complex or said AT III/heparinoid complex on said anion exchanger material in a preceding step and eluting said complex at a pH ranging from 6.0 to 7.5.

6. A method as set forth in claim 1, further comprising a virus inactivation step.

7. A method as set forth in claim 1, wherein heparin or a heparinoid is admixed with human plasma or an AT III-containing plasma fraction to form said heparin/AT III complex or said heparinoid/AT III complex, and subjecting said heparin/AT III complex or said heparinoid/AT III complex to a heat treatment so as to inactivate infectious agents at a temperature ranging from 40 to 70° C. for a period of time of between 3 and 30 hours.

8. A method as set forth in claim 7, wherein said heat treatment to inactivate infectious agents is carried out in the presence of stabilizing organic polyvalent salts.

9. A method as set forth in claim 8, wherein said stabilizing organic polyvalent salts used in said heat treatment are at least one of a citrate and an ammonium sulfate.

10. A method as set forth in claim 7, wherein said heat treatment to inactivate infections agents is carried out at a temperature around 60° C. for 10 hours.

11. A method as set forth in claim 1, wherein said starting material is one of a human plasma or a plasma fraction comprising AT III.

12. A method as set forth in claim 11, wherein said human plasma is cryoprecipitate-poor human plasma.

* * * * *